(12) United States Patent
Gardner et al.

(10) Patent No.: US 9,400,271 B2
(45) Date of Patent: Jul. 26, 2016

(54) METHOD AND APPARATUS FOR TEMPERATURE CONTROL DURING SAMPLE ANALYSIS

(71) Applicant: Thermo Scientific Portable Analytical Instruments Inc., Tewksbury, MA (US)

(72) Inventors: Craig M. Gardner, Belmont, CA (US); Michael Burka, Winchester, MA (US)

(73) Assignee: Thermo Scientific Portable Analytical Instruments Inc., Tewksbury, MA (US)

( * ) Notice: Subject to any disclaimer, the term of this patent is extended or adjusted under 35 U.S.C. 154(b) by 0 days.

(21) Appl. No.: 14/132,671

(22) Filed: Dec. 18, 2013

(65) Prior Publication Data

US 2015/0168367 A1    Jun. 18, 2015

(51) Int. Cl.
*G01N 33/22*    (2006.01)
*G01J 3/02*    (2006.01)
*G01N 21/65*    (2006.01)

(52) U.S. Cl.
CPC .............. *G01N 33/227* (2013.01); *G01J 3/027* (2013.01); *G01N 21/65* (2013.01); *G01N 2201/0221* (2013.01)

(58) Field of Classification Search
CPC ......... G01J 3/44; G01J 3/4406; G01J 3/4412; G01J 2003/4418; G01J 2003/4424
See application file for complete search history.

(56) References Cited

U.S. PATENT DOCUMENTS

| | | | |
|---|---|---|---|
| 6,046,809 A * | 4/2000 | deGroot et al. | ............... 356/337 |
| 7,450,227 B2 | 11/2008 | Dwight et al. | |
| 7,636,157 B2 | 12/2009 | Wang et al. | |
| 7,701,571 B2 | 4/2010 | Azimi et al. | |
| 7,928,391 B2 | 4/2011 | Azimi et al. | |
| 8,081,305 B2 | 12/2011 | Azimi et al. | |
| 8,107,069 B2 | 1/2012 | Wang et al. | |
| 8,241,922 B2 | 8/2012 | Murphy et al. | |
| 2007/0236697 A1 | 10/2007 | Zribi et al. | |
| 2008/0165344 A1 * | 7/2008 | Treado et al. | .................. 356/72 |
| 2008/0239306 A1 | 10/2008 | Sutherland et al. | |

(Continued)

FOREIGN PATENT DOCUMENTS

JP       11108868 A   *  4/1999
WO    2006137885 A2    12/2006

(Continued)

OTHER PUBLICATIONS

Ehlerding et al., "Resonance-Enhanced Raman Spectroscopy onExplosives Vapor at Standoff Distances," International Journal of Spectroscopy, vol. 2012, 2012, pp. 1-9.

(Continued)

*Primary Examiner* — Kara E Geisel
*Assistant Examiner* — Dominic J Bologna
(74) *Attorney, Agent, or Firm* — Ion C. Abraham

(57) ABSTRACT

A method of detecting an explosive material, and an analyzer and computer program products that may perform such methods. A method may include illuminating at least a portion of the material with light, and monitoring the temperature of the illuminated portion. T power or location of the illuminating light may be altered in response to the monitored temperature. Raman spectral data are produced in response to Raman radiation emitted from the portion in response to the light. The composition of the material may be analyzed based on the Raman spectral data or generating an indication to an operator that the material cannot be safely analyzed.

17 Claims, 3 Drawing Sheets

(56) References Cited

U.S. PATENT DOCUMENTS

| | | | |
|---|---|---|---|
| 2009/0213361 | A1 | 8/2009 | Vander Rhodes et al. |
| 2010/0191493 | A1 | 7/2010 | Brown et al. |
| 2010/0315629 | A1 | 12/2010 | Knopp et al. |
| 2011/0271738 | A1* | 11/2011 | McGill .................. G01N 21/64 73/23.41 |
| 2012/0018829 | A1* | 1/2012 | Beck et al. .................... 257/431 |
| 2012/0223130 | A1 | 9/2012 | Knopp et al. |
| 2012/0287427 | A1 | 11/2012 | Li et al. |

FOREIGN PATENT DOCUMENTS

| | | |
|---|---|---|
| WO | 2011143630 A1 | 11/2011 |
| WO | 2014008359 A1 | 1/2014 |

OTHER PUBLICATIONS

McNesby et al., "Detection and characterization of explosives using Raman spectroscopy: identification, laser heating, and impact sensitivity,"Proceedings of SPIE, vol. 3882, Jul. 23, 1997, pp. 121-135.

Moros et al., "Fundamentals of stand-off Raman scattering spectroscopy for explosive fingerprinting," Journal of Raman Spectroscopy, vol. 44, No. 1, Nov. 8, 2012, pp. 121-138.

Waterbury et al, "Fabrication and testing of a standoff trace explosivesdetection system," Chemical, Biological, Radiological, Nuclear, and Explosives (CBRNE) Sensing XII, SPIE, 1888 28th St. Bellingham WA, 98225-6785 USA, vol. 8818, No. 1, May 13, 2011, pp. 1-6.

* cited by examiner

METHOD AND APPARATUS FOR TEMPERATURE CONTROL DURING SAMPLE ANALYSIS

FIELD

This invention generally relates to identifying a material, for example a material that may be explosive.

BACKGROUND

Embodiments of the present invention make use of Raman spectral data obtained from a sample in response to illuminating the sample with light. Raman spectroscopy is an effective tool for identifying and characterizing a vast array of molecules. In Raman spectroscopy, a sample is illuminated with light typically from a laser and of a known wavelength (typically visible, or near infrared, but also ultraviolet). The laser light (also sometimes referred to as the Raman pump) interacts with the electron clouds in the molecules of the specimen and, as a result of this interaction, experiences selected wavelength shifting representing differences between the vibrational and/or rotational energy levels of the molecule. The precise nature of this wavelength shifting depends upon the molecules present in the specimen and can include both a Stokes shift (where the emitted photon is of longer wavelength than the incident or illuminating photon) and an anti-Stokes shift (where the emitted photon is of shorter wavelength than the incident photon). However, because they arise from molecules in excited vibration states, anti-Stokes spectra are lower in intensity than Stokes spectra, and also diminish in intensity with greater anti-Stokes shifts. A unique wavelength signature (typically called the Raman signature, or Raman spectrum) is produced by each molecule. This unique Raman signature permits the molecule to be identified and characterized. More specifically, the spectrum of light returning from the specimen is analyzed with an optical spectrometer so as to identify the Raman-induced wavelength shifting of the Raman pump light, and then this resulting Raman spectrum is compared (for example, by a processor) with a library of known Raman signatures so as to identify a molecule in the sample. Raman theory, including the Stokes/anti-Stokes ratio is described, for example, in D. A. Long, "Raman Spectroscopy", McGraw-Hill, 1977, particularly at pages 82-84.

Raman spectroscopy may include Surface Enhanced Raman Spectroscopy ("SERS") where the reflective surface is reflective, and enhances the Raman signal in a manner known for SERS surfaces. Principles and different techniques of SERS spectroscopy are described, for example, in US20120287427, U.S. Pat. No. 8,241,922, U.S. Pat. No. 7,450,227, WO/2006/137885, and elsewhere. In any embodiment the sample of interest may be a solid, or a fluid, such as a gas or liquid Raman spectroscopy is widely used in scientific, commercial and public safety areas. Recent technological advances have made it possible to significantly reduce the size and cost of Raman spectroscopy systems. This has in turn increased the range of practical applications for Raman spectroscopy. For example, portable units have recently become available for various field uses, such as the on-site identification of potentially hazardous substances. Details of analyzers using Raman spectroscopy and spectra interpretation can be found, for example, in U.S. Pat. No. 8,107,069, U.S. Pat. No. 8,081,305, U.S. Pat. No. 7,928,391, U.S. Pat. No. 7,701,571, U.S. Pat. No. 7,636,157, U.S. Pat. No. 8,107,069, and U.S. patent publications US2009/0213361, US2010/0191493, US2010/0315629 (all of which references are incorporated herein by reference), and elsewhere. The design of Raman spectrometers, including discussions of lasers and detectors, is also described in Richard L. McCreery, "Raman Spectroscopy for Chemical Analysis", Wiley-Interscience, 2000.

SUMMARY

Some embodiments of the present invention recognize that Raman spectroscopy can be useful for identifying materials that may be explosive. However, some embodiments also recognize that the temperature of the portion of the sample illuminated may exceed an ignition point of the material, or the change (including the rate of change) of the temperature may suggest that the ignition point may soon be reached, as a result of heating by the illuminating light. Embodiments of the present invention make use of either or both of these relationships to raise or lower the illuminating light power so that Raman spectral data can be collected until there is sufficient data to enable an analysis of the composition of the material.

The present invention provides in some embodiments, a method of detecting an explosive material. The method may include illuminating at least a portion of the material with light and monitoring the temperature of the illuminated portion. The power and/or location of the illuminating light may be altered in response to the monitored temperature. For example, the power might be increased or decreased depending on the temperature and/or the change in temperature. In any embodiment, the "change" in temperature may include the rate of change in temperature. Raman spectral data is produced in response to Raman radiation emitted from the portion in response to the light. The composition of the material may be analyzed based on the Raman spectral data and/or an indication may be generated to an operator that the material cannot be safely analyzed. For example, the operator indication may be presented on a display and/or as an audible message or warning.

Other embodiments provide a method of identifying an explosive material which include the illuminating, the producing Raman spectral data, and the analyzing of the composition of the material, as described above. In these other embodiments though, the Raman spectral data can be analyzed for an indication of the temperature and/or change in temperature of the illuminated portion. The power and/or location of the illuminating light on the portion may be altered in response to the analyzed change in Raman spectral data resulting from the temperature change.

An analyzer is also provided in other embodiments, for detecting an explosive material. The analyzer may comprise a light source, a detector, and a processor. The light source illuminates at least a portion of the material with light, while the detector detects Raman radiation emitted in response to the illuminating light. The processor may execute any one or more of the methods of the present invention.

Further embodiments provide a computer program product carrying a computer program in a non-transient form. The program, when loaded into a programmable processor controlling a light source for illuminating a material and a detector to detect Raman radiation emitted in response to illuminating light, may execute any one or more of the methods of the present invention.

DRAWINGS

Embodiments of the invention will now be described with reference to the drawings, in which.

In the Figures, the same reference numerals are used to represent the same or similar components.

DETAILED DESCRIPTION OF EMBODIMENTS

Figure 1:
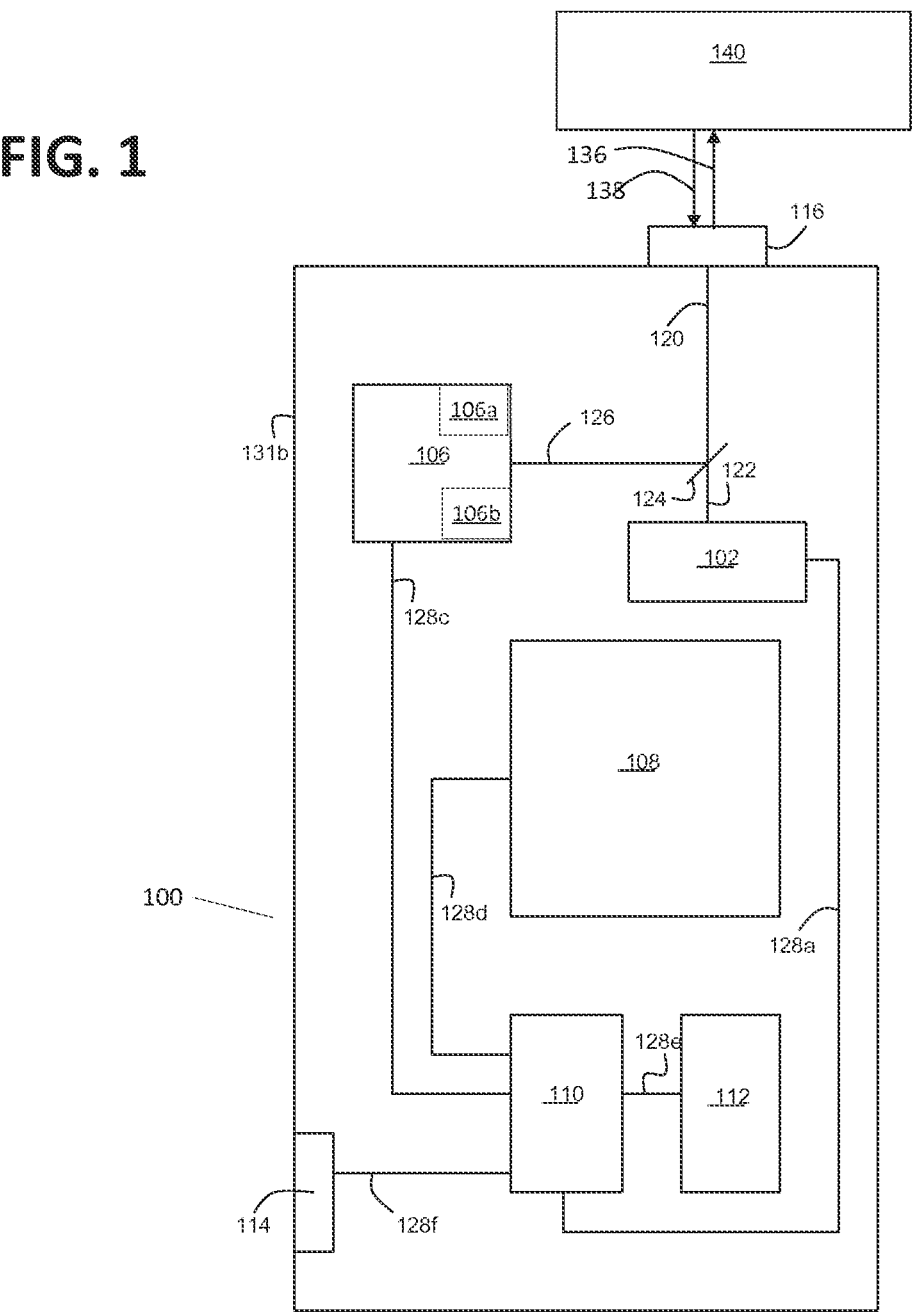
FIG. 1 is a schematic view of an analyzer of the present invention.

Any embodiment of the present invention may further include one or more of any of the features described below or anywhere throughout this application. In any embodiment, the power of the illuminating light may be altered based on a value or change (including rate of change) of a monitored temperature of the illuminated portion. For example, the temperature may be monitored directly using a remote infra-red sensor in a well known manner. Alternatively, or additionally, the monitoring may be based on a measurement such as some feature of Raman spectral data, that varies with temperature and therefore serves as an indicator of temperature. For example, a peak width (such as half-height peak width) of a Raman spectral line may be used as an indication of temperature, or a rate of change of such a feature used as an indication of rate of change of temperature. In this case the altering of illuminating light power may be based on the value or rate of change of a particular peak width.

A method may include increasing the power of the illuminating light if the value or change of the monitored temperature is within a predetermined limit. Alternatively, the power of the illuminating light may be decreased if the value or change in the temperature of the illuminated portion is beyond a predetermined limit.

Optionally, prior to increasing the power of the illuminating light, the Raman spectral data may first be evaluated as to whether it is sufficient for analyzing the composition of the material. When it is insufficient the power may then be increased. The spectral data may be determined to be insufficient if the spectral data on which an analysis may be based, have a signal/noise ratio below a predetermined limit. If that signal/noise meets or exceeds the predetermined limit, the spectral data may be determined to be sufficient for the analysis. One method for evaluating signal/noise for this purpose is described in Avraham Lorber, "Error Propagation and Figures of Merit for Quantification by Solving Matrix Equations", Annal. Chem., v. 58, n. 6, pp. 1167-1172, May 1986. In any event, in situations where it is determined that the Raman spectral data is sufficient for analyzing the composition then the illuminating light power may not be increased, and may even be turned off, and the analysis simply completed at that point.

The illuminating light may comprise laser light, and the power of the laser light may be altered. The altering of the power of the laser light, or any type of illuminating light, may be accomplished in any one or more of a number of ways. For example, the intensity of the light may be decreased, or the intensity may remain the same but the light is cycled on and off at varying on and off times, such that the time averaged power is altered. Various frequencies may be used for time averaging, such as at least 2 Hz up to 10 Hz, 50 Hz, or 100 Hz.

The temperature of the sample under analysis is a function of the light power incident on the sample, the spatial distribution of that power, the absorption coefficient of the material at the incident light wavelength, the thermal conductivity of the material, and its heat capacity. The first two of these factors can be varied to control the temperature of the illuminated portion of the sample. For example, in some embodiments the illuminating light includes multiple light pulses, such as a series of light pulses, then multiple sets of Raman spectral data may be produced following the beginning of each pulse. In this case the Raman spectral data may be summed to reduce signal/noise ratio. Sufficient time may be allowed between light pulses to allow most, or substantially all, of possible interfering optical fluorescence to decay. For example, at least 100 milliseconds, at least 10 milliseconds, or at least 1 millisecond, or as little as 100 microseconds, 10 microseconds, or 1 microsecond might be provided between the end of one pulse and the start of the next in a pulse sequence.

As mentioned previously, an analyzer of the present invention may execute any one or more of the methods of the present invention. Similarly, a computer program product of the present invention may execute any one or more of the methods of the present invention when loaded onto a processor communicating with the illuminating light source and the detector.

Any embodiment of an analyzer of the present invention may be hand-held or portable. By "hand-held" is referenced that the analyzer weighs less than 5 kg, 2, 1, or even less than 0.5 or 0.2 kg, and may have dimensions of less than 50 cm or even 30 cm in each dimension, and one of the dimensions (the thickness) may even be less than 10 cm or 5 cm or 3 cm. A "hand-held" analyzer will often be battery powered with the battery typically fitting within the foregoing dimensions and included in the foregoing weights, although a separate power supply could be provided and connected to the spectrometer. A "portable" analyzer may be somewhat larger in size, for example less than 50 kg, 20 kg or 10 kg, such as 10 to 50 kg or 20 to 50 kg, and have dimensions somewhat larger (such as up to 500, 200 or up to 100 cm in any one dimension) and typically includes a power input which connects to an external power supply (though a battery may be provided). A "portion" refers to only a part of an item, but can include all of it. For example, a "portion" of a material or object may refer to all or just a part of that material or object.

As mentioned above, methods of the present invention include any method which can be executed by any apparatus described in this application. Computer program products of the present invention include any computer program product carrying a computer program which can execute any method of the present invention. A computer program "product" is a tangible, non-transitory medium, which may carry a computer program of the present invention (for example, a magnetic, optical, or solid-state memory) in a non-transitory, but potentially temporary form (for example, the program may be erased).

Throughout the present application the following terms have the described meaning unless a usage is clearly to the contrary. Words such as "first" and "second" do not indicate any particular relationship, and are used just to distinguish similarly named elements. It will be appreciated that while different elements of embodiments of the present invention have been described separately, they could in practice use some or all of the same components. "Analysis", "analyze", or similar words, reference identifying a material as an explosive material. This "analyzing" or similar is based on Raman spectral data in the sense that Raman spectral data is used by itself, or in combination with other information or data, to aid in the identification. For example, information from a label on a container holding the material can be used along with the Raman spectral data such that the Raman spectral data provides an indication in the form of a confirmation that the material is in fact the material indicated by the label. The identification can be either or both, qualitative (for example, the material is explosive, or is an explosive of a particular type, or has a high probability of being present) or quantitative (for example, the concentration of an explosive in the material exceeds a predetermined amount, or is present in a stated amount or concentration). "Identification" references the information presented, and need not be absolutely correct. For example, a processor may determine that an explosive material is likely to be present and presents that result as an "identification" with or without additional information that the result is uncertain or has a specified degree of certainty (for example, "explosive X is present with 60% certainty"). An "explosive" material is one that will likely undergo spontaneous combustion under normal atmospheric conditions, upon an ignition event (for example, a spark) or reaching an ignition temperature. Such materials include incendiary materials and are sometimes referenced as "highly energetic materials". A "processor" is any hardware, or hardware and software combination, that can accomplish the tasks required of it. For example, a processor could include a suitably programmed general purpose microprocessor, or an application specific integrated circuit ("ASIC"), or some combination of microprocessors. In the case where the processor is programmable, it may not yet be programmed but only capable of being loaded with the program required so the processor can then accomplish the tasks required. "Light" may reference any electromagnetic radiation in the ultraviolet (100 to 400 nm), visible (400-700 nm), or infra-red (700-2000 nm) ranges. "A" or "an" means a single one of a thing and includes more than one. For example, "identifying an explosive" includes identifying one or more explosive materials in a composition. "Or" refers to any one or more of the specified items. For example, "analyzing a composition . . . or generating an indication to an operator" just analyzing, just generating the operator indication, or doing both. "May" means optionally. Sometimes "and/or" may be used but it is interchangeable with "or". For example, if any embodiment of the invention "may have feature X" then that embodiment can actually include feature X or not include feature X. When a range of any quantity is mentioned, that range specifically describes every included whole unit value within that range (for example, "up to 100 milliseconds" specifically describes values which include 1, 2, 3, 4, . . . , 100 milliseconds and the like). When a "portion" of an object or material is illuminated this usually means some part of the object or material, but includes the possibility that all of the object or material is illuminated. All references cited in the present application are fully incorporated herein by reference. However, where anything in an incorporated reference contradicts anything stated in the present application, the present application prevails. The order of any sequence of events in any method recited in the present application, is not limited to the order recited. Instead, the events may occur in any order which is logically possible, including the events occurring simultaneously where that is logically possible.

Turning now to FIG. 1, there is shown a schematic diagram of an analyzer 100 of an embodiment of the present invention. Analyzer 100 includes a light source 102 in the form of a laser, a radiation processing module 106, a display 108, a processor 110, a storage unit 112, and a communication interface 114. Processor 110 is in electrical communication with light source 102, radiation processing module 106, display 108, storage unit 112, and communication interface 114 via communication lines 128a-f. Each of these components is enclosed within a housing 131b.

In some embodiments, radiation generated by light source 102 or received from object 104 is not coupled through fibers 122, 120, 126 as shown in FIG. 1. Instead, illuminating light 136 generated by light source 102 propagates through air or space to reach port 116, where it then illuminates a portion of an object 140 which is to be analyzed for explosive material. Similarly, Raman radiation 138 emitted from object 140 in response to illuminating light 138, can enter housing 131b via port 116, and thereafter propagate through air or space to reach radiation processing module 106. In any event, Raman radiation 138 is directed toward a radiation processing module 106 by a beamsplitter 124.

Radiation processing module 106 includes a detector 106a which detects Raman radiation 138 used to determine one or more properties of the material of object 140 (or of a substance associated with object 140, such as a substance within object 140). For example, radiation processing module 106 can be configured to determine a Raman spectrum of one or more substances within object 140. The Raman spectrum is communicated to processor 110 via an electronic signal transmitted by radiation processing module 106 along communication line 128c. Similarly, radiation processing module 106 may optionally include an infra-red detector 106b to detect thermal infra-red radiation emitted by object 140. That information is also communicated by line 128c to processor 110 so that processor 110 can evaluate the temperature of the portion of the object 140 illuminated by illuminating light 136. Detector 106b is optional since, as described, detector 106a may be used to provide such information or processor 110 can use a feature in the Raman spectrum as a measure of the value or change in temperature of the illuminated portion Infra-red detector 106b is not necessarily a part of the radiation processing module 106. Rather, it might be positioned on the housing 131b close to the sample interface optics. In a Raman spectrometer that uses a fiber optic probe extending away from housing 131b at port 116, the infra-red detector might be positioned at the end of the probe, or it might be incorporated into the probe head optics. In these situations infra-red detector 106b is separate from the remainder of radiation processing module 106 that is internal to the spectrometer housing 131b.

In general, radiation processing module 106 includes various optical, mechanical, and electronic elements that can be used to analyze emitted radiation 138. For example, radiation processing module 106 can include one or more elements for dispersing electromagnetic radiation in the form of light into a plurality of component wavelengths such as gratings and/or prisms. Radiation processing module 106 can also include various lenses and/or mirrors for collimating, focusing, and re-directing EM radiation, one or more filter elements for reducing radiation intensity, and one or more beamsplitting elements for dividing a radiation beam into two beams. Radiation processing module 106 also typically includes electronic components such as radiation detectors (e.g., CCD cameras, photodiodes and/or photodiode arrays) and an electronic processor.

Storage unit 112 typically includes a re-writable persistent flash memory module. The memory module is configured to store a database that includes a library of information about various objects and/or substances. The library includes information such as Raman spectra for various substances, for example. Processor 110 can retrieve Raman spectra from storage unit 112 via a request transmitted on communication line 128e. Storage unit 112 can also store settings, predetermined limits, and other configuration information for analyzer 100 such as default scanning parameters and operating settings. Other storage media can also be included in storage unit 112, including various types of re-writable and non-rewritable magnetic media, optical media, and electronic memory.

Communication interface 114 includes a wireless transmitter/receiver unit that is configured to transmit signals from processor 110 to other devices, and to receive signals from other devices and communicate the received signals to processor 110. Typically, for example, communication interface 114 permits processor 110 to communicate with other devices—including other scanning systems and/or computer systems—via a wireless network that includes multiple devices connected to the network, and/or via a direct connection to another device. Processor 110 can establish a secure connection (e.g., an encrypted connection) to one or more devices to ensure that signals can only be transmitted and received by devices that are approved for use on the network.

Processor 110 communicates with a central computer system to update the database of information stored in storage unit 112. Processor 110 is configured to periodically contact the central computer system to receive updated database information. The updated database information can include, for example, a list of explosive substances and/or substances which are not explosives. Processor 110 can also communicate with other scanning systems to broadcast alert messages when certain substances—such as an explosive substance—is detected, for example.

Often, analyzer 100 is a portable analyzer. In that case housing 131b has a hand-held form factor and, as a hand-held device, can be used in a wide variety of applications. Housing 131b is a rugged housing that protects the various components of analyzer 100 against breakage if housing 131b is dropped or otherwise subjected to trauma by the system operator. To ensure that housing 131b is a rugged housing, the housing includes shock-absorbing inserts that reduce the strength of external forces applied to components of analyzer 100. Housing 131b can also include shock-absorbing external pads (e.g., formed of rubber) to cushion forces that are generated during rough handling. Even with these features, the total mass of analyzer 100 may be less than 3 kg.

For ergonomic handling of system 100, housing 131b can include a handle or a gripping portion to allow a system operator to comfortably manipulate the system. Alternatively, or in addition, in some embodiments, housing 131b can include contours that facilitate handling of analyzer 100 with only one hand.

Figure 2:
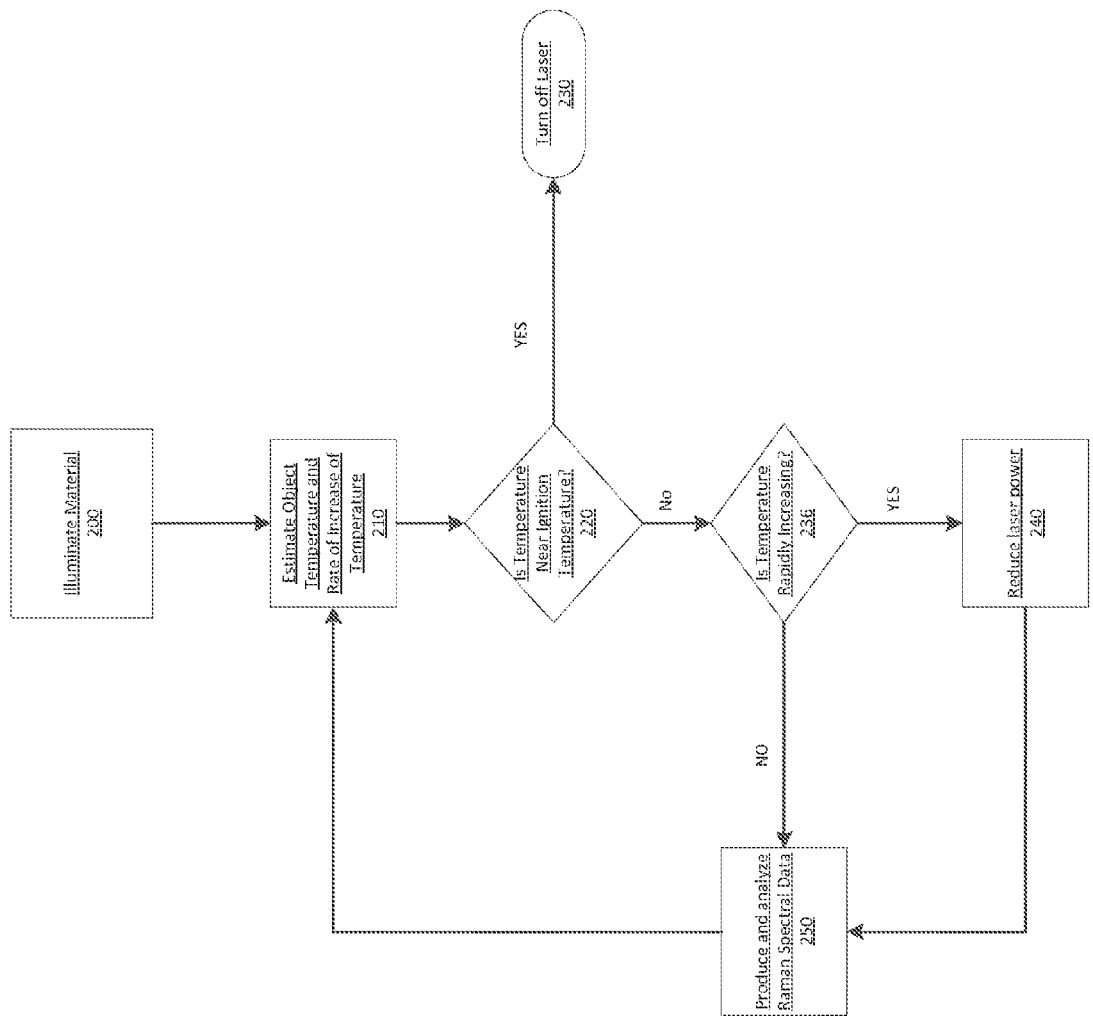
FIG. 2 is a flowchart illustrating a method of an embodiment of the present invention.

Referring now to FIG. 2, a method of the present invention is illustrated which may be performed by analyzer 100. A portion of the object 140 to be tested for explosive material is illuminated (200) by illuminating light 136 from light source 102 which is under control of processor 110. The temperature and rate of increase of the temperature of the object 140 is estimated (210). This can be from data obtained from an infra-red temperature detector 106b of analyzer 100, or can be replaced by an analysis of collected Raman spectral data that is responsive to temperature changes (such as a peak width) in a manner already described. If the temperature is near a suspected ignition temperature of an explosive material (220) then the laser can be turned off (230) to avoid igniting the material. If this is not the case but the temperature is rapidly increasing at a rate beyond a predetermined limit (236), or the Raman spectral data change resulting from a temperature change is changing at a rate beyond a predetermined limit (236), then the power of the illuminating light is reduced (240). If the temperature or spectral data are not beyond the predetermined limit (236) then Raman spectral data can be produced or continued to be produced, and analyzed (250). Processes (210-250) are continued until sufficient data has been collected to make the analysis, at which point light source 102 is turned off and the result is presented on display 108.

It will be appreciated that in FIG. 2, as in other embodiments, the illustrated processes are not necessarily in the order shown. For example, all of processes (210-250) other than turning off the laser (230), may be running simultaneously.

Figure 3:
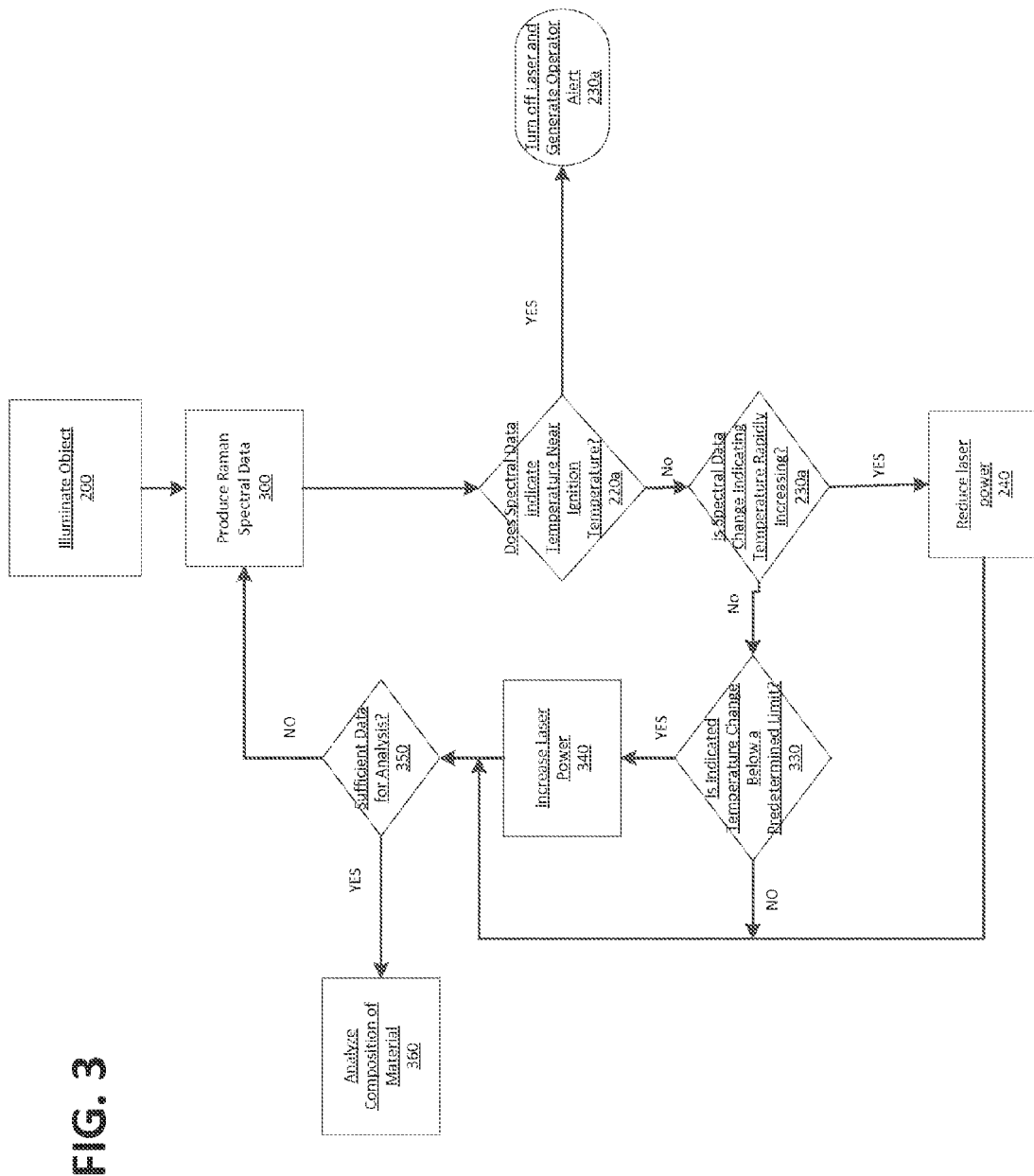
FIG. 3 is a flowchart illustrating a method of another embodiment of the present invention.

In the embodiment of FIG. 3, a portion of object 104 is illuminated as in FIG. 2. In this embodiment Raman spectral data production (200) starts essentially immediately upon turning on the light source 102. Processes (220a, 230a) are the same as (220, 230) of FIG. 2 except the value and rate of change of one or more features of the Raman spectral data which change with temperature (such as a half-height peak width), may be used as an indication of temperature and the rate of change of temperature. However, the data from infra-red detector 106b could replace the use of Raman spectral data as an indication of the value or rate of change of the temperature of the illuminated portion of object 104, in any one or all of the processes in FIG. 3 where the Raman spectral data is used for that purpose. Also, in the embodiment of FIG. 3, if the rate of change is below a predetermined limit (330) then the illuminating light power may be increased (340). Increasing illuminating light power can allow sufficient Raman spectral data for an analysis to be collected in less time. Once sufficient data for analysis has been collected (350) then light source 102 is turned off, an analysis is completed (360), and the result presented on display 108. If sufficient data has not been collected for an analysis (350) then processes (300-360) may be continued until sufficient data has been collected. At any point when the spectral data indicates temperature is near an ignition temperature light source 102 can be turned off and an operator alert generated (230a).

Examples of different auto-ignition temperatures include: HMX (a nitramine explosive)—279° C.; Trinitrotoluene (TNT, a nitroaromatic explosive)—502° C.; Nitrocellulose—180° C.; Nitroglycerine—170° C.; Smokeless powder—160° C. Auto-ignition temperatures for other explosives are widely available throughout the literature. An example of a rate of change in temperature that might be used may be 10° C./sec as a threshold for too fast a rise and a rise of 1° C./sec as an indication that power can be increased. These are guideline figures and larger or smaller values may be used in either case. Note that auto-ignition of explosives is a function of both temperature and rate of temperature increase and also varies with exact formulation, so all numbers are approximate.

Particular embodiments of the present invention have been described in detail above. However, it will be apparent that variations and modifications of the described embodiments are possible. For example, light source 102 could also be turned off if it is found at process (230) or (230a) that the rate of change exceeds a second predetermined limit which is higher than the predetermined limit already mentioned for reducing the light source power. Accordingly, the present invention is not limited by the embodiments described.

We claim:

1. A method of detecting an explosive material, comprising:
    illuminating at least a portion of the material with light;
    monitoring the temperature of the illuminated portion, said monitoring including analyzing a change or a rate of change in thermal infra-red radiation resulting from a temperature change at the portion caused by the illumination, said analyzing including monitoring a rate of change in a peak width in Raman spectral data;

altering the power or location of the illuminating light in response to the monitored temperature;

producing Raman spectral data in response to Raman radiation emitted from the portion in response to the light;

analyzing the composition of the material based on the Raman spectral data or generating an indication to an operator that the material cannot be safely analyzed.

2. A method according to claim 1 wherein the time averaged power of the illuminating light is altered.

3. A method according to claim 2 wherein the time averaged power of the illuminating light is increased if the value or change of the monitored temperature is below a predetermined limit.

4. A method according to claim 2 wherein the time averaged power of the illuminating light is decreased if the value or change of the monitored temperature is beyond a predetermined limit.

5. A method according to claim 2 wherein the illuminating light comprises laser light.

6. A method according to claim 2 wherein the time averaged power of the illuminating light is altered by cycling the light on and off for different durations.

7. A method according to claim 2 wherein the time averaged power of the illuminating light is altered by altering the intensity of the illuminating light.

8. An analyzer for detecting an explosive material, comprising:
    a light source to illuminate at least a portion of the material with light;
    a detector to detect Raman radiation emitted in response to the light;
    a processor which:
    produces Raman spectral data in response to Raman radiation emitted from the portion in response to the light;
    monitors a temperature at the illuminated portion, said monitoring including analyzing a change or a rate of change in thermal infra-red radiation resulting from a temperature change at the portion caused by the illumination, said analyzing including monitoring a rate of change in a peak width in Raman spectral data;
    alters the power or location of the illuminating light on the portion in response to the monitored temperature; and
    analyzes the composition of the material based on the Raman spectral data or generates an indication to an operator that the material cannot be safely analyzed.

9. An analyzer according to claim 8 wherein the processor increases the power of the illuminating light if the value or rate of change in the monitored temperature is within a predetermined limit.

10. An analyzer according to claim 8 wherein the processor decreases the power of the illuminating light if the value or rate of change in the monitored temperature is beyond a predetermined limit.

11. An analyzer according to claim 8 wherein the light source comprises a laser light.

12. An analyzer according to claim 8 wherein the processor alters the time averaged power of the illuminating light.

13. An analyzer according to claim 12 wherein the processor alters the time averaged power of the illuminating light by cycling the light on and off for different durations.

14. An analyzer according to claim 12 wherein the processor alters the time averaged power of the illuminating light by altering the intensity of the illuminating light.

15. A computer program product carrying a computer program in a non-transient form, wherein the program when loaded into a programmable processor controlling a light source for illuminating a material and a detector to detect Raman radiation emitted in response to illuminating light, executes the method of:
    illuminating at least a portion of the material with light;
    producing Raman spectral data in response to Raman radiation emitted from the portion in response to the light;
    monitoring a temperature at the illuminated portion, said monitoring including analyzing a change or a rate of change in thermal infra-red radiation resulting from a temperature change at the portion caused by the illumination, said analyzing including monitoring a rate of change in a peak width in Raman spectral data;
    altering the power or location of the illuminating light on the portion in response to the temperature; and
    analyzing the composition of the material based on the Raman spectral data or generating an indication to an operator that the material cannot be safely analyzed.

16. A computer program product according to claim 15 wherein the computer program increases the power of the illuminating light if the value or rate of change the monitored temperature is within a predetermined limit.

17. A computer program product according to claim 15 wherein the computer program determines that the Raman spectral data is insufficient for analyzing the composition of the material, prior to increasing the power of the illuminating light.

* * * * *